US010631808B2

(12) United States Patent
Proksa et al.

(10) Patent No.: US 10,631,808 B2
(45) Date of Patent: Apr. 28, 2020

(54) GENERATING A LUNG CONDITION MAP

(71) Applicant: KONINKLIJKE PHILIPS N.V., Eindhoven (NL)

(72) Inventors: Roland Proksa, Neu Wulmstorf (DE); Jens Von Berg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 97 days.

(21) Appl. No.: 15/763,909

(22) PCT Filed: Sep. 30, 2016

(86) PCT No.: PCT/EP2016/073390
§ 371 (c)(1),
(2) Date: Mar. 28, 2018

(87) PCT Pub. No.: WO2017/055527
PCT Pub. Date: Apr. 6, 2017

(65) Prior Publication Data
US 2018/0271465 A1 Sep. 27, 2018

(30) Foreign Application Priority Data
Sep. 30, 2015 (EP) .................................. 15187525

(51) Int. Cl.
A61B 6/00 (2006.01)
G06T 7/00 (2017.01)
(Continued)

(52) U.S. Cl.
CPC ............. A61B 6/50 (2013.01); A61B 6/461 (2013.01); A61B 6/484 (2013.01); A61B 6/5217 (2013.01);
(Continued)

(58) Field of Classification Search
CPC . G06T 7/0012; G06T 7/11; G06T 7/50; G06T 2207/10116; G06T 2207/30061;
(Continued)

(56) References Cited

U.S. PATENT DOCUMENTS 8,204,292 B2  6/2012  Knapp et al. ................. 382/132
8,903,153 B2  12/2014  Von Berg et al. ..... G06T 7/0083
(Continued)

FOREIGN PATENT DOCUMENTS

WO  WO2011/077334 A1  6/2011  ............... G06T 7/00
WO  WO2014002026 A1  1/2014  ............ G01N 23/04
WO  WO2014202705 A1  12/2014  ............... G06T 7/00

OTHER PUBLICATIONS

S. Schleede El Al: "Emphysema Diagnosis Using X-Ray Dark-Field Imaging at a Laser-Driven Compact Synchrotron Light Source", Proceedings of the National Academy of Sciences, vol. 109, No. 44, Oct. 16, 2012 (Oct. 16, 2012), pp. 17880-17885, XP055260851.
(Continued)

Primary Examiner — Andrew W Johns
(74) Attorney, Agent, or Firm — Larry Liberchuk

(57) ABSTRACT

A biomarker of lung condition can conventionally be obtained using a spirometer. A spirometer provides an estimate of the volume of air expelled by the lungs. This is a rather indirect biomarker of the staging of a lung condition, because a reduction in lung volume may only manifest itself at a point where symptoms are well advanced. A lung condition such as Chronic Obstructive Pulmonary Disorder (COPD) is typically not visible on conventional X-ray attenuation images, because the relevant tissue (alveoli-bearing microstructured lung tissue) contains a lot of air. The X-ray dark-field can successfully indicate microstructure, such as lung alveoli. Therefore, imaging the lungs using the dark-field can provide information on the status of COPD.

14 Claims, 5 Drawing Sheets

(51) Int. Cl.
G06T 7/50 (2017.01)
G06T 7/11 (2017.01)

(52) U.S. Cl.
CPC .......... *A61B 6/5252* (2013.01); *G06T 7/0012* (2013.01); *G06T 7/11* (2017.01); *G06T 7/50* (2017.01); *A61B 6/482* (2013.01); *G06T 2207/10116* (2013.01); *G06T 2207/30061* (2013.01)

(58) Field of Classification Search
CPC .......... A61B 6/484; A61B 6/50; A61B 6/5252; A61B 6/5258; A61B 6/5294
See application file for complete search history.

(56) References Cited

U.S. PATENT DOCUMENTS

| 9,805,467 | B2 | 10/2017 | Maack et al. ......... G06T 7/0012 |
| 2009/0052754 | A1* | 2/2009 | Goto et al. ............. A61B 5/055 382/128 |
| 2015/0187096 | A1* | 7/2015 | Baturin et al. .......... G01T 1/164 382/132 |

OTHER PUBLICATIONS

Marcus J Kitchen et al: "Phase Contrast Image Segmentation Using a Laue Analyser Crystal", Physics in Medicine and Biology, Institute of Physics Publishing, Bristol GB, vol. 56, No. 3, Jan. 6, 2011 (Jan. 6, 2011), pp. 515-534, XP020203787.
Felix G. Meinel et al: "Diagnosing and Mapping Pulmonary Emphysema on X-Ray Projection Images: Incremental Value of Grating-Based X-Ray Dark-Field Imaging", PLOS One, vol. 8, No. 3 , Mar. 26, 2013 (Mar. 26, 2013), p. e59526, XP055260858.
Bech, M. et al., "In-Vivo Dark-Field and Phase-Contrast X-Ray Imaging", Scientific Reports, 3.: 3209, 2013.
Matsuoka, S. et al., "Quantitative CT Assessment of Chronic Obstructive Pulmonary Disease", Radiographics, 30(1), 55-66, 2010.
Von Berg, C. et al., "A Novel Bone Suppression Method that improves Lung Nodule Detection", International Journal of Computer Assisted Radiology Surgery, Apr. 2016, vol. 11, (4):641-55.
Meinel, F. et al., "Improved Diagnosis of Pulmonary Emphysema Using In Vivo Dark-Field Radiography", Investigative Radiology, vol. 49, No. 10, pp. 653-658, Oct. 2014.
Yaroshenko, A. et al., "Preclinical X-Ray Dark-Field Radiography for Pulmonary Emphysema Evaluation", 2013 IEEE 10th International Symposium on Biomedical Imaging, pp. 370-373 , 2013.
Yaroshenko, A. et al., "Pulmonary Emphysema Diagnosis with a Preclinical Small-Animal X-Ray Dark Field Scatter-Contrast Scanner", Radiology: vol. 269: No. 2, pp. 427-433, Nov. 2013.
Aroshenko, A. et al., "Small-Animal Dark-Field Radiography", Medical Imaging, Medical Imaging 2014: Physics of Medical Imaging, 2014 Proc. of SPIE, vol. 9033.
Schwab, f. et al. "Comparison of Contrast-to-Noise Ratios of Transmission: Grating Based X-Ray Dark Field Imaging of Lung Tissue", Med. Phys. 23 (2013) 236-242.

* cited by examiner

GENERATING A LUNG CONDITION MAP

FIELD OF THE INVENTION

The present invention relates to an apparatus for generating a lung condition map, an X-ray imaging arrangement, a method for generating a lung condition map, a computer program product, and a computer-readable medium.

BACKGROUND OF THE INVENTION

When an X-ray penetrates an object of interest, information about the structure of the object of interest is conveyed in the form of attenuation, phase, and scatter components of the X-ray. Conventional detectors integrate the scatter and phase changes, so that the attenuation image does not display the phase or scatter information. Recent interferometric approaches have made it possible to derive the phase and scatter components of the X-ray image, and so more information about the structure of an imaged object of interest can be obtained.

Dark-field scattering refers to the process of an X-ray beam being scattered due to microstructure in an object of interest. The dark-field effect normally is not visible, because a conventional attenuation X-ray image effectively acts to perform a line integration of the scattered X-rays. With a specially adapted interferometer placed before the X-ray detector, a scattering component of the X-ray radiation may be separated from an attenuation radiation and a phase modulated component.

WO 2014/002026 A1 discusses a method for dark-field imaging including acquiring dark-field image projections of an object with an imaging apparatus. Such imaging methods can, however, be further improved.

SUMMARY OF THE INVENTION

It would be advantageous to have an improved technique for providing diagnostic information based on X-ray images.

Towards this end, a first aspect of the invention provides an apparatus for generating a lung condition map.

The apparatus comprises an input unit, and a processing unit.

The input unit is configured to provide to the processing unit X-ray attenuation information of a patient's chest, and X-ray dark-field information of a patient's chest.

The processing unit is configured to segment the X-ray attenuation information to provide segmented X-ray image data separated from unsegmented areas. The segmented image data comprises a lung mask image corresponding to a lung structure region in the X-ray attenuation information. The processing unit is also configured to provide boneless lung image data by applying a bone suppression algorithm to the lung mask image, and to generate a lung depth map by applying a radiation attenuation model to the boneless lung image data.

The lung depth map comprises a lung thickness value for each data value of the boneless lung image data. The processor is also configured to normalize data values of the X-ray dark-field information with spatially corresponding data values of the lung depth map, to yield normalized lung dark-field information representing a lung condition map.

According to a second aspect of the invention, there is provided an X-ray imaging arrangement comprising:
an X-ray image acquisition device with an X-ray source and an X-ray detector; and
an apparatus as previously described.

The X-ray image acquisition device is configured to acquire X-ray attenuation information and X-ray dark-field information of the chest of a patient, and to provide the X-ray attenuation information and the X-ray dark-field information to an interface of the apparatus. According to a third aspect of the invention, there is provided a method for generating a lung condition map, comprising the following steps:
a) providing X-ray attenuation information of a patient's chest;
b) providing X-ray dark-field information of a patient's chest;
c) segmenting the X-ray attenuation information to provide segmented X-ray image data separated from unsegmented areas, wherein the segmented image data comprises a lung mask image corresponding to a lung structure region in the X-ray attenuation information;
d) providing boneless lung image data by applying a bone suppression algorithm to the lung mask image;
e) generating a lung depth map by applying a radiation attenuation model to the boneless lung image data, wherein the lung depth map comprises a lung thickness value for each data value of the boneless lung image data; and
f) normalizing data values of the X-ray dark-field information with spatially corresponding data values of the lung depth map, to yield normalized lung dark-field information representing a lung condition map.

According to a fourth aspect of the invention, there is provided a computer program product comprising instructions for controlling a device as previously described, or an X-ray imaging arrangement as previously described, which, when being executed by a processing unit, is adapted to perform the method steps as previously described.

According to a fifth aspect of the invention, there is provided a computer-readable medium having stored the computer program product of the previous description.

Many lung disorders are difficult to identify using conventional X-ray attenuation imaging techniques. This is because the structural changes to the lung of the patient implied by many lung disorders do not present themselves until the disease is an advanced stage. Human lungs are microstructured, so that the lung surface area is maximized, allowing efficient gas exchange. The microstructure comprises thin-walled sacs called alveoli. Changes in the distribution or size of the alveoli in the lung could indicate the presence of a disease. For example, a number of alveoli may collapse, to form a single large one. This condition is called emphysema.

Therefore, the use of an X-ray imaging modality which is sensitive to changes in alveoli size enables an earlier detection of lung conditions, which may be a biomarker for a lung disorder. In addition, because a variation of the disorder may be distributed over the lung, it is possible to obtain an image of the distribution of the disorder over the extent of the lung.

This is an improvement on previous lung disorder detection techniques, which often use a device such as a spirometer. A spirometer can provide information on the overall capacity of a lung, but cannot localize the condition of a lung disorder to a particular part of a lung. A spirometer also cannot identify lung disorders before they present themselves with the symptom of breathing difficulty. Therefore, the subject-matter of the claims provides an improved lung condition assessment tool.

In the following description, the term "X-ray attenuation information" refers to X-ray information providing an image in which the intensity of the image is proportional to the integral of the transmission properties (determined by density, material permittivity, etc) of a volume of tissue through which the X-ray has propagated. In other words, X-ray attenuation information is a classical X-ray image.

In the following description, the term "X-ray dark-field information" refers to X-ray information containing the scattering component of an applied X-ray. Typically, this can be obtained using an interferometric detection approach, but other approaches are known. Microstructures in an object of interest can cause scattering of an X-ray wave. Classically, the scattering component has been integrated into a final X-ray attenuation value, and hence has not been separable. Using interferometric X-ray imaging techniques, for example, it is now possible to distinguish the scatter component of the X-ray signal from the attenuation and phase components, to provide extra information about the internal structure of an object of interest.

The term "lung mask image" refers to a region of an X-ray attenuation image which contains attenuation information representing the structure of a lung, when the chest is imaged as an object of interest.

The term "boneless lung image data" refers to a section of a lung mask image which has had image information caused by the presence of bones in the region of interest removed by a bone suppression algorithm. Such bones may be the scapula, or rib cage bones.

The term "lung depth map" refers to a set of information, most commonly a two-dimensional bit map image, in which the magnitude of each pixel of the bit map reflects the thickness (in millimetres, for example) of a region of a lung at that pixel.

The term "radiation attenuation model" refers to a mathematical technique or algorithm which uses radiation physics to calculate the attenuation of an X-ray beam when the X-ray beam propagates through a certain thickness of soft tissue, or lung tissue. A radiation attenuation model may model the soft tissue as water, and may model the interior space of a lung as air. A region of soft tissue may thus be defined as causing an appreciable amount of X-ray attenuation, whereas a section of lung containing air may be defined as causing an almost zero attenuation. The radiation attenuation model may be inverted, and may simulate the attenuation that would result if a certain thickness of lung was filled with water. In this way, a lung mask image may be used to generate a thorax image in which the lung tissue appears not to be present.

The term "normalized lung dark-field information" refers to the output of a process to normalize the dark-field information to account for the thickness of the lungs. Thicker portions of the lung will cause more scattering to take place. This is the case because, for a unit of distance, assuming constant scattering takes place per unit distance, the X-ray beam will have propagated through the lung for more units of distance, and so will have incurred more scatter. The normalization of the lung dark-field information to the thickness of the lung prevents this from providing inaccurate lung condition map results.

The term "lung condition map" is, for example, a 2D image containing information about at least the condition of the microstructure of a lung, in the absence of effects caused by chest bones, or variations in lung thickness. Thus, the lung condition map may provide a clinician with extra useful information about the condition of a lung.

In other words, an idea of the invention is to provide a new tool for presenting the condition of lung microstructure to a clinician, using an X-ray exposure.

These, and other, aspects of the present invention will become apparent from, and be elucidated with reference to, the embodiments described hereinafter.

DETAILED DESCRIPTION OF EMBODIMENTS

Lung conditions, such as chronic obstructive pulmonary disorder, are difficult to detect using a non-invasive technique. In chronic obstructive pulmonary disease (COPD), the normally small and compact microstructure of the alveoles begins to collapse into each other, and become larger. The current histological method for COPD classification, for example the classification of emphysema, is the so-called mean chord length (MCL). This is a statistical measure comprising the mean alveole wall to alveole wall distance. The alveole condition is, typically, not visible on conventional attenuation X-rays. The air-sac structure of alveoli means that they cause very little attenuation to an X-ray beam, and thus are not visible in X-ray attenuation images until a COPD condition has reached a severe state.

Thus, in a typical clinical situation, obtaining an actual measurement of the MCL for a live patient would imply an invasive biopsy procedure, which will rarely be attempted. Attempts to track the progress of COPD thus usually involve the use of a spirometer to provide an indirect estimate of the damage to a patient's breathing capacity caused by the degradation of the alveoles.

Figure 1:
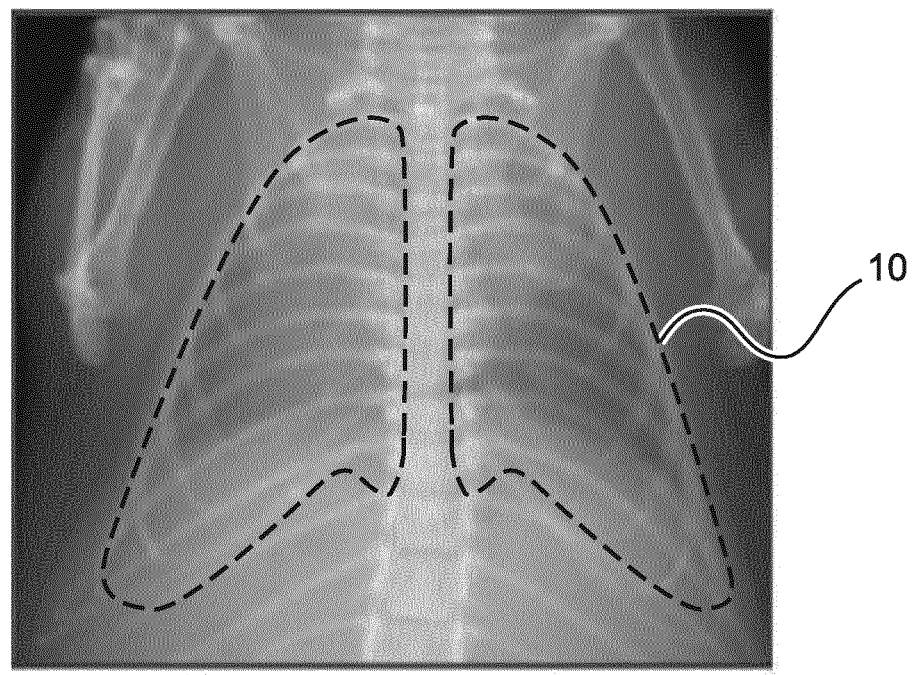
FIG. 1 shows an attenuation X-ray image of the thorax of a small mammal.

FIG. 1 shows a classical attenuation-based X-ray image of the thorax of a mouse affected by COPD. By convention, denser areas in the image have a lighter appearance. Although this mouse suffered from severe COPD at the time of taking the image, it is not evident from FIG. 1 that the mouse suffered from COPD The area of the thorax containing the lungs shown by the dotted line 10 has no unusual components, in comparison to the lungs of a healthy mouse.

A recent technique for obtaining more information from an X-ray image relies on the use of the X-ray dark-field.

The problem of the relatively weak absorption of human alveoli can be addressed using dark-field imaging. Dark-field imaging generates images based on the scatter components of the X-ray radiation diffracted by microstructures in the scanned object. X-ray dark-field effect is exploited to reveal microstructure of alveoli, and thus provide new information about the lung structure.

Figure 2:
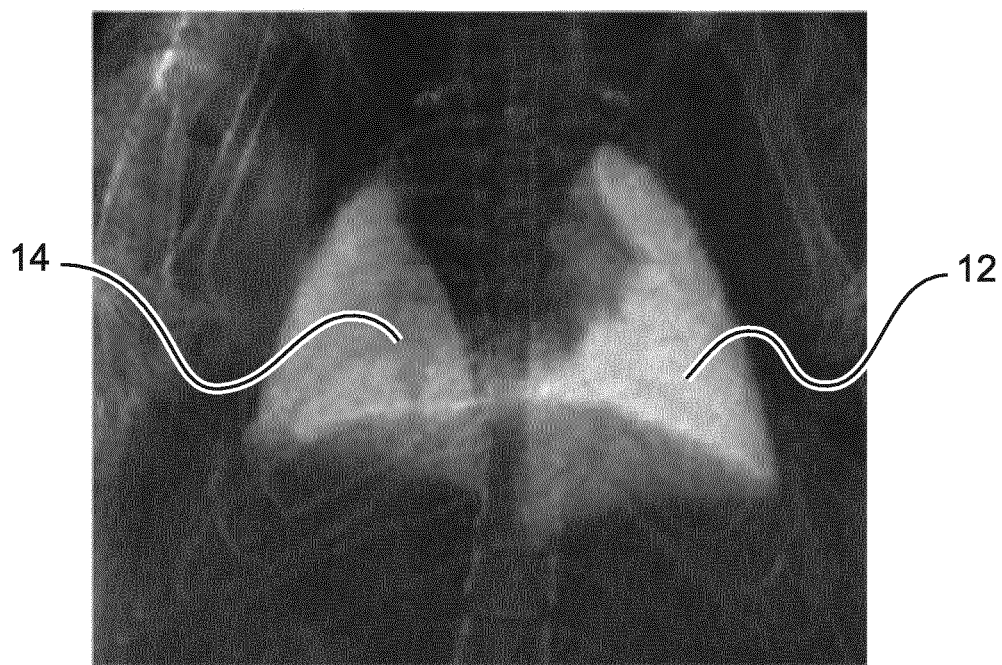
FIG. 2 shows a dark-field image of the thorax of the same small mammal.
Figure 3:
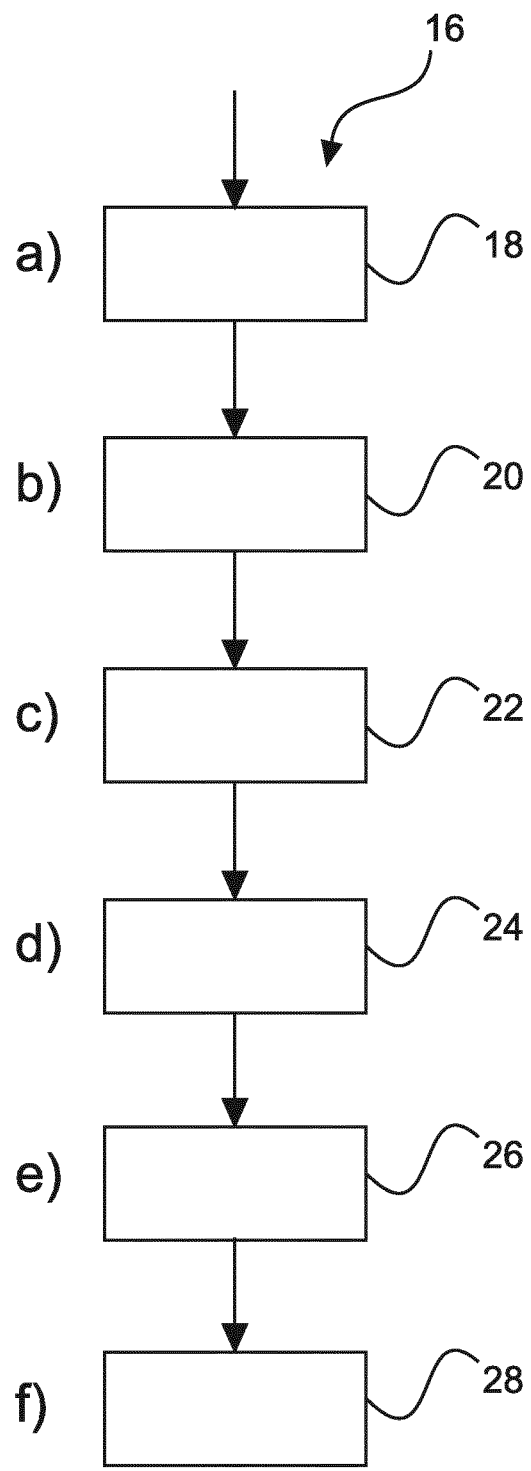
FIG. 3 shows a method according to an aspect of the invention.

FIG. 2 shows a dark-field X-ray image of the same scene as in FIG. 1. It is seen that there is a high signal level over the lung field. The internal microstructure of the lung alveoli has caused a lot of X-ray radiation to scatter. It can be seen that the right-hand side lung 12 is slightly brighter than the left-hand side lung 14. Thus, to a first approximation, the microstructure of the alveoli in the right-hand side lung 12 is likely to be denser than the microstructure of the alveoli in the left-hand side lung 14. In other words, the mean chord length (MCL) of the alveoli in the right-hand side lung 12 is likely to be shorter than the mean chord length of the alveoli for the left-hand side lung 14. Thus, the dark-field signal correlates well with certain lung conditions connected with the degradation of the alveoli, thus allowing diseases such as COPD to become accessible with dark-field imaging. According to a third aspect of the invention, there is provided a method 16 for generating a lung condition map, comprising the following steps:

a) providing 18 X-ray attenuation information of a patient's chest;
b) providing 20 X-ray dark-field information of a patient's chest;
c) segmenting 22 the X-ray attenuation information to provide segmented X-ray image data separated from unsegmented areas, wherein the segmented image data comprises a lung mask image corresponding to a lung structure region in the X-ray attenuation information;
d) providing 24 boneless lung image data by applying a bone suppression algorithm to the lung mask image;
e) generating 26 a lung depth map by applying a radiation attenuation model to the boneless lung image data, wherein the lung depth map comprises a lung thickness value for each data value of the boneless lung image data;
f) normalizing 28 data values of the X-ray dark-field information with spatially corresponding data values of the lung depth map, to yield normalized lung dark-field information representing a lung condition map.

According to the third aspect of the invention, it is possible to track the development of COPD in its early stages, when the change in MCL is not discernible using an X-ray attenuation image. Thus, it is possible to provide a new biomarker, useful to a clinical professional for subsequent COPD assessment and staging.

The method will be further explained as follows:

In step a), an item of X-ray attenuation information of a patient's chest is provided. The X-ray attenuation information may be, optionally, a greyscale bitmap image provided by a digital flat panel X-ray detector, or, alternatively, may be a digitized analogue X-ray attenuation slide.

In step b), an item of X-ray dark-field information of a patient's chest is provided. The X-ray dark-field information is provided by a dark-field capable X-ray imaging arrangement. It will be appreciated that multifunction X-ray imaging apparatuses are available, enabling the simultaneous acquisition of X-ray attenuation information and X-ray dark-field information.

Optionally, a dual-mode X-ray imaging apparatus capable of capturing X-ray attenuation information and X-ray dark-field imaging information may be used to provide the X-ray attenuation information and the X-ray dark-field information. This means that the X-ray attenuation information will already be optimally registered to the X-ray dark-field information.

In step c), a segmentation algorithm is applied to the X-ray attenuation information, to provide segmented X-ray image data separated from unsegmented areas, wherein the segmented image data comprises a lung mask image corresponding to a lung structure region in the X-ray attenuation information.

Figure 4:
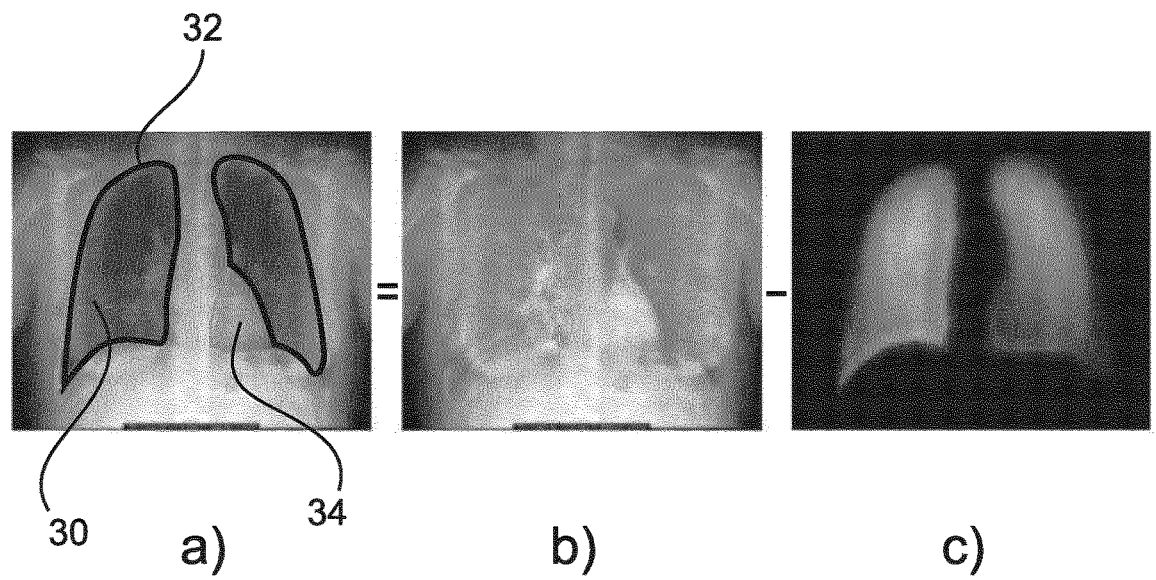
FIG. 4 shows a schematic representation of the thorax of a patient.

FIG. 4 gives an example of a process to remove bone information from a thorax attenuation X-ray.

FIG. 4c) shows a lung depth map provided, for example, by simulating a water-filled lung after a radiation attenuation model has been applied to boneless lung image data.

FIG. 4b) shows a lung attenuation image with a boneless lung field.

In FIG. 4a), the X-ray attenuation image of a human thorax has been segmented. The segmented image data 30 lying inside the segmentation contour 32 corresponds to a lung structure region in the X-ray attenuation information. Thus, it is possible to form a lung mask image. Segmentation techniques are known to those skilled in the art of image processing and will not be further discussed here. The lung depth map can be used to normalize the X-ray dark-field within the boneless lung field.

Figure 5:
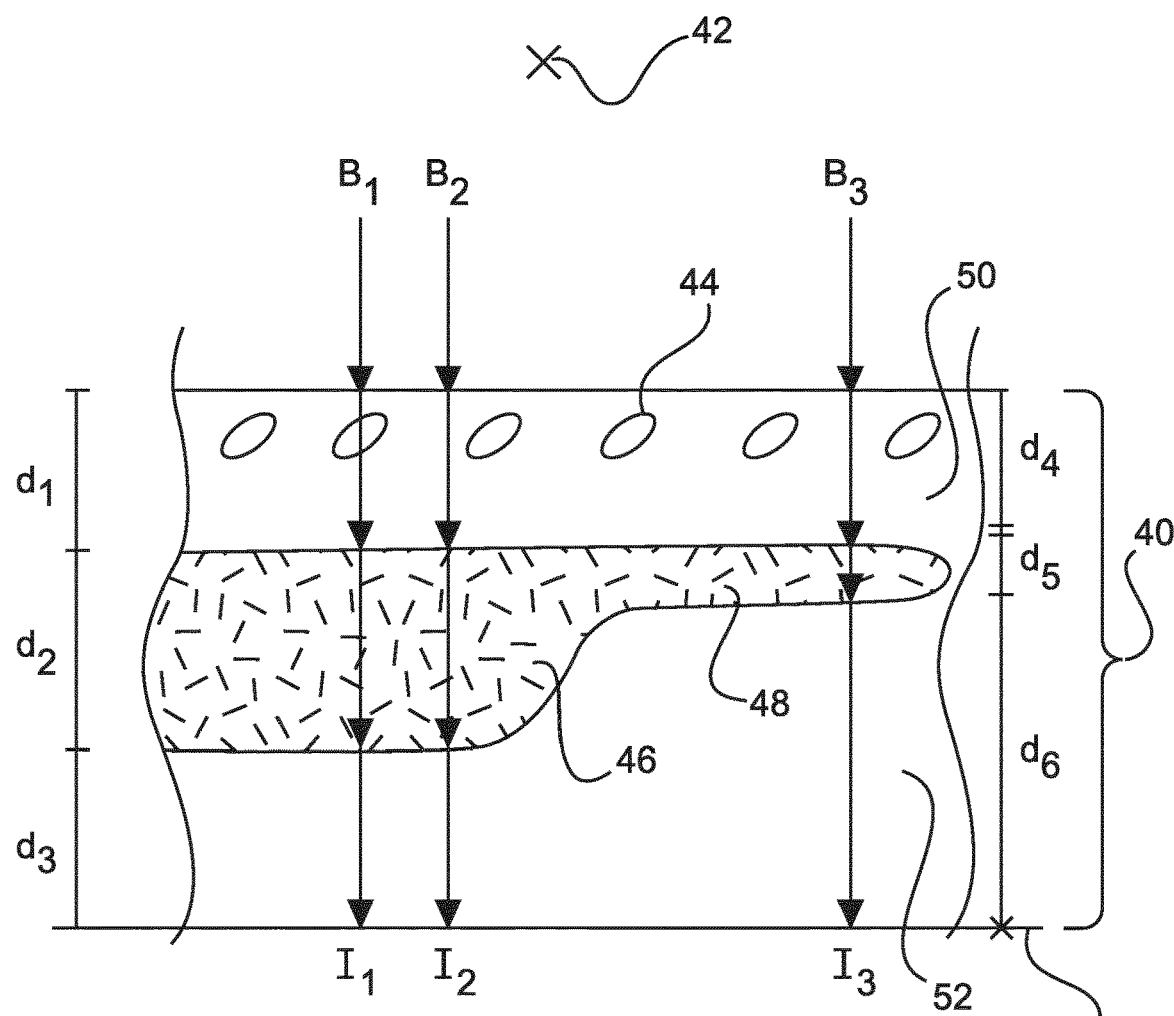
FIG. 5 shows practical information from three stages of an example of the method.

FIG. 5 shows a schematic form of a slice through a human chest cavity 40.

A schematic location of an X-ray source 42 is shown above the chest cavity 40. The chest cavity comprises rib bones 44, a section of thick lung tissue 46, a section of thin lung tissue 48, a section of upper thorax 50, and a section of lower thorax 52.

It may be assumed for the purpose of this schematic diagram that the X-ray source 42 emits uniform X-rays towards the thorax 40, and that these rays propagate through the chest cavity 40 until they are received at a flat-panel detector 54 which may be X-ray film or a digital flat panel detector. It is noted that the interferometric apparatus used for dark-field detection is not shown in the schematic diagram for simplicity, but would be present in an X-ray detector capable of detecting the dark-field.

The upper thorax has a thickness $d_1$ and/or $d_4$. The thick side of the lung 46 has a thickness $d_2$. The thin side of the lung has a thickness $d_5$. The lower thorax 52 has a thickness $d_3$ and $d_6$. A first ray $B_1$ is shown penetrating the upper thorax 50, and being attenuated by a rib bone and to a lesser extent by tissue in the upper and lower thorax. The ray $B_1$ is also attenuated to a degree in the thick section of the lung 46 before detection at the flat panel detector. It is noted that rays $B_1$ to $B_3$ may represent either X-ray attenuation, or dark field paths.

The ray $B_2$ follows a similar route through the thorax to $B_1$, although $B_2$ will be larger in magnitude at $I_2$ because it does not propagate through a dense rib bone.

Ray $B_3$ would also undergo a similar degree of attenuation caused by the upper and lower thorax to $B_1$, and is not attenuated by a rib bone. In this illustrated situation, rays $B_2$ and $B_3$ will appear to have approximately the same attenuation, even though they travel through sections of lung with different thicknesses.

The reason for this is that lungs contain mostly air, and air does not attenuate an X-ray to the degree that water-containing soft tissue does. However, if it is assumed that the lung has a uniformly dense microstructure, it will be appreciated that the ray $B_2$ will experience much greater dark-field scattering, because the ray $B_2$ will have propagated through a much greater distance of microstructured material, compared to $B_3$.

Although the staging of COPD can be linked to the increase in alveoli size caused by COPD, in order for COPD to be reliably diagnosed in such a situation, the thickness of the lung should be decoupled from the overall presence of microstructure, or microstructure changes in the lung.

To remove the lung bone areas 44, a bone suppression algorithm is applied to the lung mask image. Bone suppression algorithms have been discussed in, for example, WO 2011/077334, and U.S. Pat. No. 8,903,153. Such techniques have already shown advantages in detecting lung nodules by removing rib shadows, for example.

Optionally, the X-ray attenuation information is detected with a dual energy detector, which enables bone to be distinguished from soft-tissue without further processing. Then, the bone suppression algorithm becomes a matter of distinguishing pixels of the X-ray attenuation information caused by photons of X-rays having a higher or lower energy.

According to another option, a bone suppression algorithm is provided according to WO 2011/077334 in which a source image gradient field is smoothed using Gaussian kernels. A smoothing unit is adapted for correcting the source image gradient vector orientation before smoothing. This approach averages the source image gradient field along lines perpendicular to a contour normal of a rib bone, and parallel to the contour, preserving sharp bone edges along the contour. Another bone-removal approach is one employing a feature extraction method, and a neural network-based regression, as in the method described in U.S. Pat. No. 8,204,292.

Of course, it will be appreciated by the person skilled in the art that many bone suppression algorithms may be provided, and are suitable for this technique, provided their result in a lung mask image being presented which does not comprise bone shadows.

The detected dark-field projection image gives the line integral of the number of alveoli wall interfaces present through a lung for a specific detector pixel. Therefore, normalization of this integral to a pixel specific lung tissue length, or to a pixel specific lung tissue attenuation gives a mean biomarker measure per pixel of the input images. The lung depth $d_2$ or $d_5$ is estimated using an image processing method that achieves signal separation after acquisition of the X-ray attenuation and X-ray dark-field image information.

Thus, following segmentation of the projection image, an artificial attenuation image is constructed, where the pixels inside the segmented lung structure region in the X-ray attenuation information are modified so that the lungs appear invisible, following the techniques described in WO 2011/077334. Alternative techniques may be used for the removal of the lung information. For example, the technique in WO 2014/202705 proposes to generate a lung thorax mask which shows the thorax structure without lung tissue, and this approach is also applicable.

The artificial attenuation image is effectively an image in which each pixel is a proxy for the depth of the imaged lung, at the space represented by a specific pixel. In other words, the artificial attenuation image can be considered to be a lung depth map.

Then, data values of the X-ray dark-field information are normalized with spatially corresponding data values of the lung depth map, to yield normalized lung dark-field information representing a lung condition map. In other words, for every pixel of the lung depth map, a corresponding pixel in the lung dark-field information is selected. Then, this lung dark-field measure is divided by the lung thickness value at the corresponding lung depth map pixel.

Repeating this process for all pixels in the lung dark-field information generates a lung condition map, in which the lung dark-field effect is expressed in a manner which is normalized to the lung thickness.

According to an embodiment of the invention, a method is provided as described previously, wherein in step c), the segmentation is performed on the basis of the X-ray attenuation information.

Therefore, the lung structure region is defined solely on the basis of the appearance of the lung in the attenuation image. This enables a simpler segmentation process.

According to an embodiment of the invention, in step c), the segmentation is performed on the basis of the X-ray attenuation information, and upon the basis of the X-ray dark-field information.

As discussed, a finer microstructure in the lungs causes the lungs to appear brighter in an X-ray dark-field image. Therefore, the use of the X-ray dark-field information in composing the segmentation can improve the conformity of the segmentation to the lung tissue.

According to an embodiment of the invention, in step a) and step b), the X-ray attenuation information and the X-ray dark field information are provided as separate exposures. In step b), there is the step b1) of registering the X-ray dark field information to the X-ray attenuation information.

In this embodiment, X-ray attenuation information of a patient may be provided from a separate X-ray scanner, compared to the X-ray dark-field information. Two-dimensional image registration techniques are used to align the dark-ray field information with the attenuation information. Therefore, older X-ray attenuation images may be used to provide an enhanced estimate of the lung segmentation.

According to an embodiment of the invention, the method as previously described is provided, further comprising the step h) of displaying the lung disorder map.

As will be appreciated by the person skilled in the art, the lung disorder map may be displayed as a two-dimensional image in which each pixel represents the intensity of the normalized lung dark-field information.

Optionally, the lung disorder map may comprise a "heat-map", with bright areas representing regions of the lung which are suffering from a high degree of COPD, and with dark regions of the heat map representing regions of the lung suffering from a low degree of COPD, or using another brightness, colour scheme, or contour-map display approach.

According to another embodiment of the invention, a method is provided as described previously, further comprising the step i1) of generating a lung disorder distribution of the X-ray attenuation information values against their corresponding X-ray dark-field information values; and i2) displaying the lung disorder distribution on a scatter plot.

Figure 6:
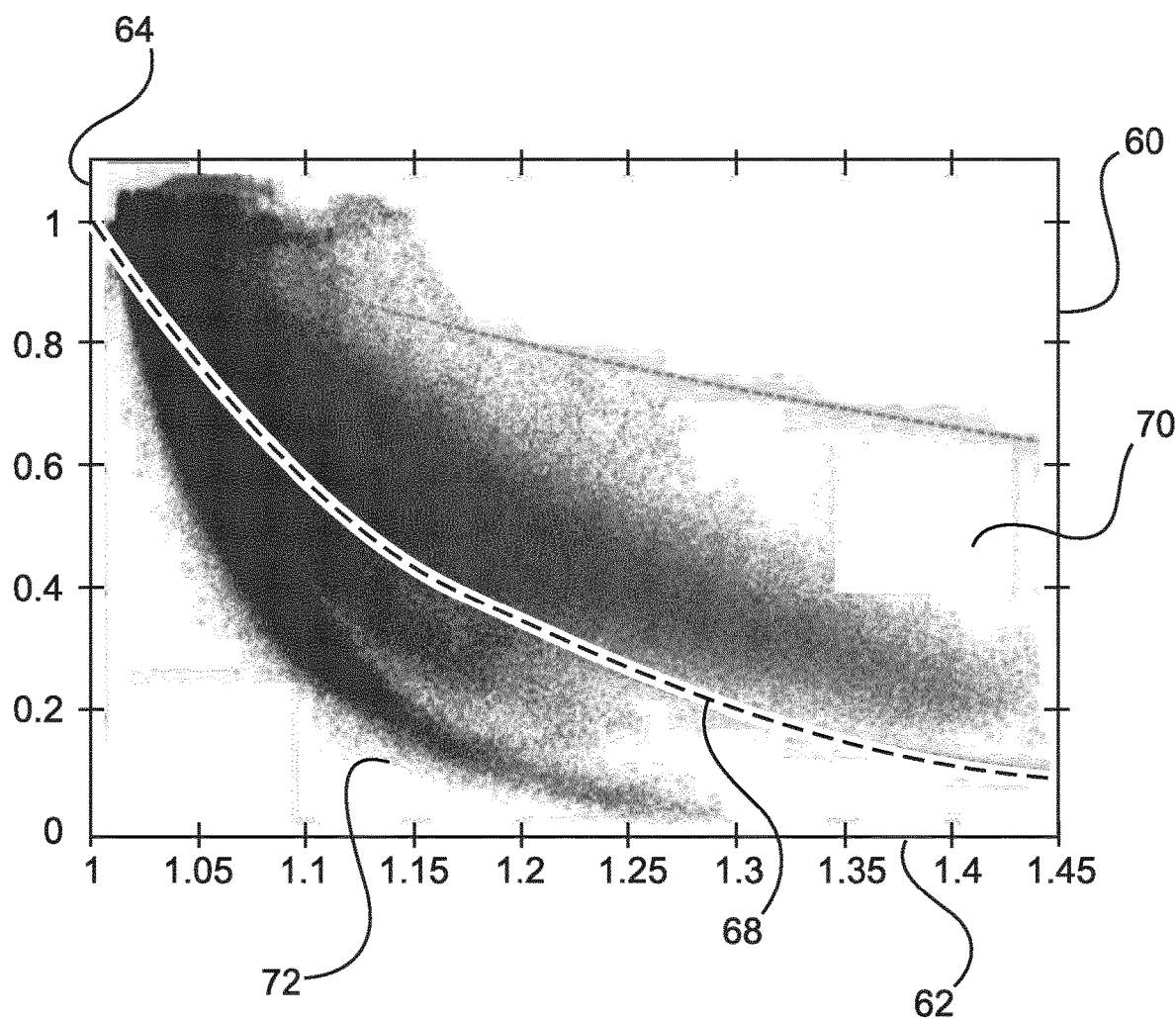
FIG. 6 shows a lung condition distribution on a scatter plot.

FIG. 6 shows a lung disorder distribution on a scatter plot 60. The scatter plot has an x-axis 62 showing relative X-ray transmission values. The y-axis 64 shows the X-ray dark-field signal in Volts. The line 68 represents the ratio ln(W)/ln(T) as a discriminator line. If most points from a lung analysis lie over the line, then the presence of COPD is indicated. Thus, such a plot is a method of distinguishing lungs suffering from COPD from the lungs of healthy subjects. Pixel values plotted underneath the line 72 may be taken to represent pixel values taken from a healthy subject.

According to an embodiment of the invention, a method is provided as described previously, further comprising the step a1) providing a lung condition map calibration table comprising a relationship between a range of X-ray dark-field information values, and the likelihood of the X-ray dark-field information values representing a lung condition; the step g1) of calibrating the lung condition map using the lung condition calibration information; and the step h1) of displaying the lung condition map.

According to this embodiment of the invention, it is possible to use experimental data to stage specific occurrences COPD by calibrating the dark-field information to experimentally-derived lung COPD metrics.

According to an embodiment, there is provided a method as described previously, wherein in step a), the X-ray attenuation information is provided as a posterior-anterior image. In step b), the X-ray dark-field information is provided as a posterior-anterior image. In step g), the lung condition map is provided as a local comparison of the left and right lungs, and/or the upper and lower lungs.

According to this embodiment of the invention, it is possible to obtain staging information of a lung condition or COPD when the effect is localized to certain lung lobes.

According to an embodiment, there is provided a method as described previously, wherein in step a), the X-ray attenuation information is provided as an anterior-posterior image. In step b), the X-ray dark-field information is provided as an anterior-posterior image.

According to an embodiment, there is provided a method as described previously, wherein in step a), the X-ray attenuation information is provided as a lateral image. In step b), the X-ray dark-field information is provided as a lateral image.

In conclusion, an approach has been described where the lung fields are segmented in the projection image (using either attenuation or attenuation and scatter radiograms). An artificial attenuation image is constructed, where the lung field pixels are modified so the lungs appear invisible following techniques described previously. The modification required to build this artificial image gives an estimate of the local lung depth. This local lung depth may be used to normalize the local dark-field signal to give a mean chord length, the biomarker for early COPD staging or detection.

The X-ray dark-field can successfully indicate microstructure, such as lung alveoli. Therefore, imaging the lungs using the dark-field can provide information on the status of COPD. As COPD progresses, the alveoli will become larger, and the dark-field signal will become weaker.

According to a first aspect of the invention, there is provided an apparatus 80 for generating a lung condition map. The apparatus comprises an input unit 82 and a processing unit 84.

Figure 7:
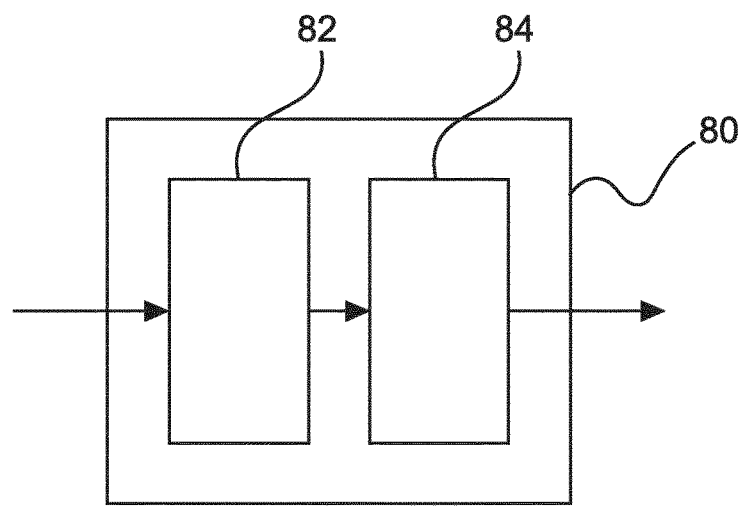
FIG. 7 shows an apparatus for generating a lung condition map according to an aspect of the invention.

FIG. 7 illustrates an example of an apparatus 80 for generating a lung condition map.

The input unit 82 is configured to provide X-ray attenuation information of a patient's chest, and to provide X-ray dark-field information of a patient's chest to the processing unit.

The processing unit 84 is configured to segment the X-ray attenuation image to provide segmented X-ray image data separated from unsegmented areas, wherein the segmented image data comprises a lung mask image corresponding to a lung structure region in the X-ray attenuation information, to provide boneless lung image data by applying a bone suppression algorithm to the lung mask image, to generate a lung depth map by applying a radiation attenuation model to the boneless lung image data.

The lung depth map comprises a lung thickness value for each data value of the boneless lung image data, the processing unit is also configured to normalize data values of the X-ray dark-field information with spatially corresponding data values of the lung depth map, to yield normalized lung dark-field information representing a lung condition map.

According to an embodiment of the invention, an apparatus 80 is provided as previously described, wherein the processor 84 is configured to perform the segmentation on the basis of the X-ray attenuation information.

According to an embodiment of the invention, an apparatus is provided 80 as previously described wherein the processor 84 is configured to perform the segmentation on the basis of the X-ray dark field information. Alternatively, the processor 84 may be configured to perform the segmentation on the basis of the X-ray dark-field information and the X-ray attenuation information.

According to an embodiment of the invention, an apparatus 80 as previously described is provided, wherein the input unit 82 is configured to provide the X-ray attenuation information and the X-ray dark field information as separate exposures; and wherein the processing unit 84 is configured to register the X-ray dark field information and the X-ray attenuation information.

According to an embodiment of the invention, an apparatus 80 is provided, according to the previous description, further comprising an output unit, and wherein the output unit is configured to display the lung condition map.

According to an embodiment of the invention, an apparatus 80 is provided as described previously, wherein the processing unit 84 is further configured to generate a lung condition distribution of the X-ray attenuation information values against corresponding X-ray dark field information values, and wherein the output unit is further configured to display the lung condition distribution on a scatter plot.

According to an embodiment of the invention, an apparatus 80 as previously described is provided, wherein the input unit 82 is further configured to provide a lung condition map calibration table comprising a relationship between a range of X-ray dark field information values, and a likelihood of the X-ray dark field information values representing a lung condition.

The processing unit 84 is further configured to calibrate the lung condition map using the lung condition calibration information, and the output unit is further configured to display the lung condition map.

According to an embodiment of the invention, an apparatus 80 as described previously is provided, wherein the input unit 82 is further configured to provide the X-ray attenuation information as a posterior-anterior image, and to provide the X-ray dark-field information as a posterior-anterior image, and wherein the processing unit 84 is further configured to provide the lung condition map as a local comparison of a left lung with a right lung, and/or of an upper lung section with a lower lung section.

According to the second aspect of the invention, an X-ray imaging arrangement 90 is provided. The X-ray imaging arrangement comprises an X-ray imaging acquisition device 92 with an X-ray image source 94 and an X-ray detector 96.

The X-ray imaging arrangement 90 also comprises an apparatus 98 as described previously.

The X-ray image acquisition device is configured to acquire X-ray attenuation information and X-ray dark-field information of the chest of a patient, and to provide the X-ray attenuation information and the X-ray dark-field information to an input of the apparatus.

Therefore, an X-ray imaging arrangement is provided which is able to provide a novel biomarker suitable for staging COPD.

Figure 8:
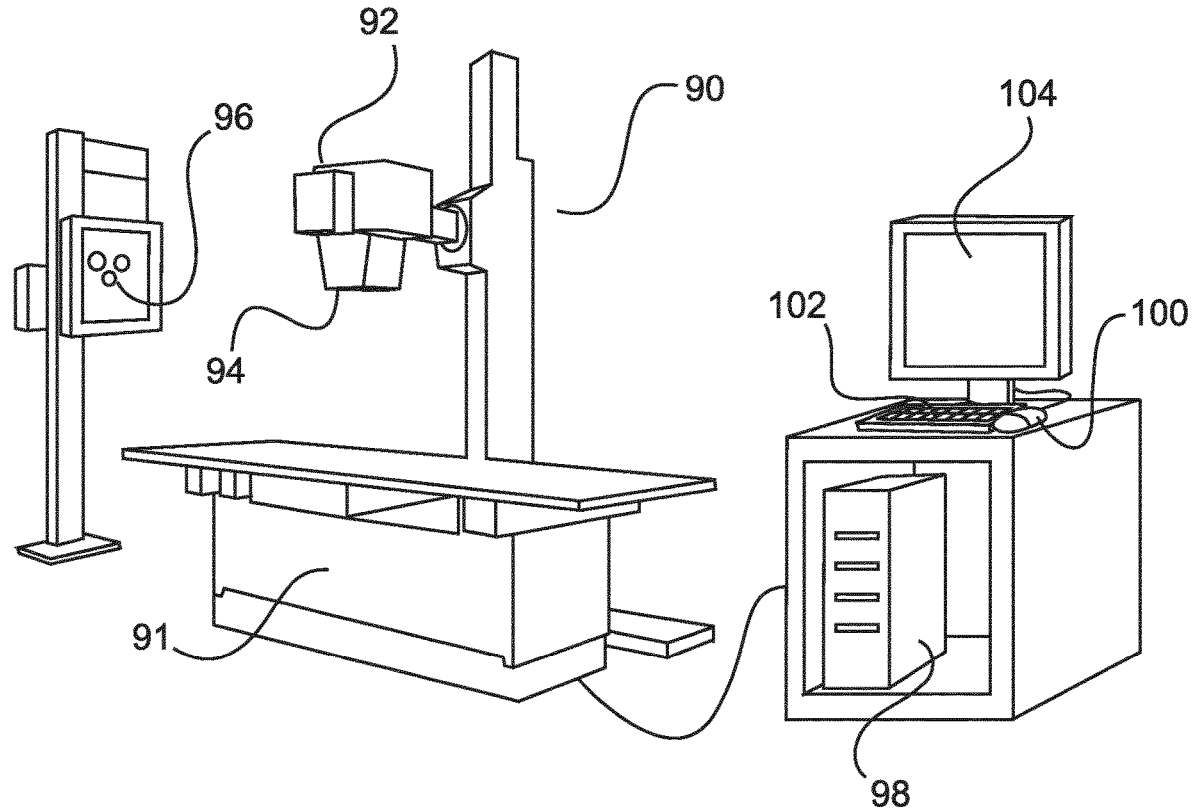
FIG. 8 shows an X-ray imaging arrangement according to an aspect of the invention.

FIG. 8 shows an X-ray imaging arrangement 90 according to the second aspect of the invention. The X-ray imaging arrangement 90 has an X-ray imaging acquisition arrangement 92 comprising an X-ray source 94 and an X-ray detector 96. In the illustrated example, the X-ray source 94 is provided on a rotatable mounting, to enable the imaging of a patient lying on the bed 91 (the bed 91 can also be provided with an X-ray detector). The X-ray source 94 may be swivelled to a horizontal position, and aimed towards the X-ray detector 96 mounted on a stand, to enable the imaging of a patient in the standing position.

The illustrated example of the X-ray imaging arrangement 90 also has an apparatus 98 according to the pre-described apparatus 80, or its embodiments, with an output (not shown) connected to the X-ray source 94 (for exposure control) and an input (not shown) connected to the X-ray detector 96 for receiving the incoming X-ray attenuation information or X-ray dark-field information. The X-ray attenuation and X-ray dark field image data from the X-ray detector 96 may be encoded in an image processing format known to a person skilled in the art.

Optionally, the X-ray attenuation information and/or X-ray dark-field information may be received as data coming from a data communication bus, or alternatively data storage means.

In an embodiment, the apparatus 98 is connected to a mouse 100 and a keyboard 102 for command input, and a display screen 104 for result viewing.

The X-ray imaging arrangement may be provided with an output means to output data, such as a hard disk, magnetic tape, a flush memory, or an optical disk (not shown). Alternatively, information may be output to a display device such as a computer monitor 104. A person skilled in the art will understand that there are many ways to connect input devices to the X-ray imaging arrangement and output devices to the output connectors of an X-ray imaging arrangement. These ways comprise, but limited to, a wired and wireless connection, a digital network such as, but not limited to, a Local Area Network (LAN) and, the Internet, and a digital, or analogue telephone network.

In an embodiment of the invention, the apparatus 80 according to the previous description may be provided as a personal computer.

In use, the X-ray image acquisition device 92 is positioned opposite the X-ray detector 96. A patient will be arranged in between the X-ray image acquisition device 92 and the X-ray detector 96. An object of interest will be imaged, in such a way as to obtain X-ray attenuation information and X-ray dark-field information, which will be input to the apparatus 98 for further processing.

According to an embodiment of the invention, the X-ray attenuation information may be downloaded from a database or an archive.

According to a fourth aspect of the invention, there is provided a computer program product comprising instructions for controlling an apparatus as previously described, or an X-ray imaging arrangement according to the previous description, which, when being executed by a processing unit, is adapted to perform the method steps as previously described.

According to a fifth aspect of the invention, there is provided a computer-readable medium having stored the computer program product as previously described. A computer program element might therefore be stored on a computer unit, which might also be an embodiment of the present invention. This computing unit may be adapted to perform or induce performance of the steps of the method described above. Moreover, it may be adapted to operate the components of the above-described apparatus.

The computing unit can be adapted to operate automatically and/or execute orders of a user. A computer program may be loaded into the working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention. A computer program may be stored and/or distributed on a suitable medium, such as an optical storage medium, or a solid state medium supplied together with, or as part of other hardware, but may also be distributed in other forms, such as via the Internet or other wired or wireless telecommunication systems.

However, the computer program may also be presented over a network like the World Wide Web, and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An apparatus for generating a lung condition map, comprising:
    an input unit configured to provide X-ray attenuation information and X-ray dark field information of a patient's chest; and
    a processor configured to:
        segment the X-ray attenuation information to provide segmented X-ray image data separated from unsegmented areas, wherein the segmented image data comprises a lung mask image corresponding to a lung structure region in the X-ray attenuation information;

provide boneless lung image data by applying a bone suppression algorithm to the lung mask image;

generate a lung depth map by applying a radiation attenuation model to the boneless lung image data, wherein the lung depth map comprises a lung thickness value for each data value of the boneless lung image data; and normalize data values of the X-ray dark field information with spatially corresponding data values of the lung depth map in order to yield normalized lung dark-field information representing a lung condition map.

2. The apparatus according to claim 1, wherein the processor is configured to perform the segmentation on the basis of the X-ray attenuation information.

3. The apparatus according to claim 1, wherein the processor is configured to perform the segmentation on the basis of the X-ray dark field information.

4. The apparatus according to claim 1, wherein the input unit is configured to provide the X-ray attenuation information and the X-ray dark field information as separate exposures; and wherein the processor is configured to register the X-ray dark field information and the X-ray attenuation information.

5. The apparatus according to claim 1, wherein
the lung condition map is displayed.

6. The apparatus according to claim 1, wherein the processor is further configured to generate a lung condition distribution of the X-ray attenuation information values against corresponding X-ray dark field information values; and wherein the lung condition distribution is displayed on a scatter plot.

7. The apparatus according to claim 1, wherein the input unit is further configured to provide a lung condition map calibration table comprising a relationship between a range of X-ray dark field information values and a likelihood of the X-ray dark field information value representing a lung condition; wherein the processor is further configured to calibrate the lung condition map using the lung condition map calibration table; and wherein the lung condition map is displayed.

8. The apparatus according to claim 1, wherein the input unit is further configured to provide the X-ray attenuation information as a posterior-anterior image, and to provide the X-ray dark field information as a posterior-anterior image; and wherein the processor is further configured to provide the lung condition map as a local comparison of a left lung with a right lung, or of an upper lung section with a lower lung section.

9. An X-ray imaging system, comprising:
an X-ray image acquisition device with an X-ray source and an X-ray detector, wherein the X-ray image acquisition device is configured to acquire X-ray attenuation information and X-ray dark-field information of a patient's chest; and an apparatus comprising a processor configured to:
segment the X-ray attenuation information to provide segmented X-ray image data separated from unsegmented areas, wherein the segmented image data comprises a lung mask image corresponding to a lung structure region in the X-ray attenuation information;

provide boneless lung image data by applying a bone suppression algorithm to the lung mask image;

generate a lung depth map by applying a radiation attenuation model to the boneless lung image data, wherein the lung depth map comprises a lung thickness value for each data value of the boneless lung image data; and normalize data values of the X-ray dark field information with spatially corresponding data values of the lung depth map in order to yield normalized lung dark-field information representing a lung condition map.

10. A method for generating a lung condition map, comprising:
providing X-ray attenuation information of a patient's chest;

providing X-ray dark field information of the patient's chest;

segmenting the X-ray attenuation information to provide segmented X-ray image data separated from unsegmented areas, wherein the segmented image data comprises a lung mask image corresponding to a lung structure region in the X-ray attenuation information;

providing boneless lung image data by applying a bone suppression algorithm to the lung mask image;

generating a lung depth map by applying a radiation attenuation model to the boneless lung image data, wherein the lung depth map comprises a lung thickness value for each data value of the boneless lung image data; and normalizing data values of the X-ray dark field information with spatially corresponding data values of the lung depth map in order to yield normalized lung dark-field information representing a lung condition map.

11. The method of claim 10, wherein the X-ray attenuation information and the X-ray dark field information is provided as separate exposures; and further comprising registering the X-ray dark field information to the X-ray attenuation information.

12. The method of claim 10, further comprising displaying the lung condition map.

13. The method of claim 10, further comprising:
providing lung condition calibration information comprising a relationship between a range of X-ray dark field information values and the likelihood of a X-ray dark field information value representing a lung condition;

calibrating the lung condition map using the lung condition calibration information; and displaying the lung condition map.

14. A non-transitory computer readable medium having one or more executable instructions stored thereon, which when executed by a processor, cause the processor to perform a method for generating a lung condition map, the method comprising:
providing X-ray attenuation information of a patient's chest;

providing X-ray dark field information of the patient's chest;

segmenting the X-ray attenuation information to provide segmented X-ray image data separated from unsegmented areas, wherein the segmented image data comprises a lung mask image corresponding to a lung structure region in the X-ray attenuation information;

providing boneless lung image data by applying a bone suppression algorithm to the lung mask image;

generating a lung depth map by applying a radiation attenuation model to the boneless lung image data, wherein the lung depth map comprises a lung thickness value for each data value of the boneless lung image data; and normalizing data values of the X-ray dark field information with spatially corresponding data values of the lung depth map in order to yield normalized lung dark-field information representing a lung condition map.

\* \* \* \* \*